(12) United States Patent
Nho et al.

(10) Patent No.: US 8,227,512 B2
(45) Date of Patent: Jul. 24, 2012

(54) PHARMACEUTICAL COMPOSITION CONTAINING DAURINOL FOR THE PREVENTION AND TREATMENT OF CANCERS

(75) Inventors: Chu Won Nho, Gangneung-si (KR); Kyung Su Kang, Gangneung-si (KR); Saet Byoul Lee, Daejeon (KR); Batsuren Dulamjav, Ulaanbaatar (MN); Tunsag Jigjidsuren, Ulaanbaatar (MN)

(73) Assignee: Korea Institute of Science and Technology, Seoul (KR)

( * ) Notice: Subject to any disclaimer, the term of this patent is extended or adjusted under 35 U.S.C. 154(b) by 245 days.

(21) Appl. No.: 12/529,828

(22) PCT Filed: Oct. 10, 2007

(86) PCT No.: PCT/KR2007/004945
§ 371 (c)(1),
(2), (4) Date: Sep. 3, 2009

(87) PCT Pub. No.: WO2008/146989
PCT Pub. Date: Dec. 4, 2008

(65) Prior Publication Data
US 2010/0105769 A1   Apr. 29, 2010

(30) Foreign Application Priority Data
May 30, 2007 (KR) .......................... 10-2007-0052890

(51) Int. Cl.
*A61K 31/35* (2006.01)
*A61P 35/00* (2006.01)
(52) U.S. Cl. ........................................ 514/464; 435/375
(58) Field of Classification Search .................. None
See application file for complete search history.

(56) References Cited

U.S. PATENT DOCUMENTS
5,627,195 A   5/1997   Hu

OTHER PUBLICATIONS

Jain, F.K.., Science (1996), 271: 1079-1080. Delivery of molecular medicine to solid tumors.*
Dermer, G.B., Bio/Technology (1994). 12: 320. Another anniversary for the war on cancer.*
Yousef, et al., Two arylnaphthalene lignans from Haplophyllum buxbaumii, Phytochemistry, 1990, 29(8):2659-2661.
Ulubelen et al., Cytotoxic lignans from Haplophyllum species, Pure & Applied Chemistry, 1994, 66 (10/11)2379-2382.
Ulubelen, Alkaloids from haplophyllum buxbaum II, Phytochemistry, 1985, 24(2):372-374.

* cited by examiner

*Primary Examiner* — Michele Flood
(74) *Attorney, Agent, or Firm* — Lucas & Mercanti, LLP (57) ABSTRACT

The present invention relates to a pharmaceutical composition for the prevention and treatment of cancer comprising daurinol as an active ingredient, more precisely a pharmaceutical composition for the prevention and treatment of cancer comprising daurinol isolated from the medicinal plant of Mongolia, *Haplophyllum dauricum* or *Haplophyllum cappadocicum*, as an active ingredient. Daurinol can selectively block the S phase of cancer cell cycle to disturb the cycle and induce apoptosis stepwise, resulting in anticancer effect. Therefore, daurinol of the present invention can be used as a positive control chemical in the research and development field of cancer biology especially for cancer therapy and prevention. Daurinol also can be a promising candidate for a novel cell cycle blocker and a novel apoptosis inducer which could be effectively used for the prevention and treatment of cancer in the end.

3 Claims, 9 Drawing Sheets

PHARMACEUTICAL COMPOSITION CONTAINING DAURINOL FOR THE PREVENTION AND TREATMENT OF CANCERS

CROSS-REFERENCE TO RELATED APPLICATIONS

This application is a 371 of PCT/KR2007/004945 filed on Oct. 10, 2007, which claims the benefit of Korean Patent Application No. 10-2007-0052890 filed on May 30, 2007, the contents of each of which are incorporated herein by reference.

TECHNICAL FIELD

The present invention relates to a pharmaceutical composition for the prevention and treatment of cancer comprising daurinol as an active ingredient, more precisely a pharmaceutical composition for the prevention and treatment of cancer comprising daurinol isolated from the medicinal plant of Mongolia, *Haplophyllum dauricum*, or *Haplophyllum cappadocicum*, as an active ingredient.

BACKGROUND ART

An anticancer agent is the general term for the drugs that directly interact with DNA of cancer cell to interrupt replication, transcription and translation at the cancer cells or intervene between the metabolism pathway to interrupt the synthesis of nucleic acid precursor and to inhibit cancer cell division to bring anticancer effect which means toxicity against cancer cells. The anticancer agent is a kind of proliferation-dependent drug which works for active proliferating cells only. So, the anticancer agent can be classified as the antiproliferative drug. Especially, cell cycle arrest and apoptosis are the two most important mechanisms of an anticancer agent for its cytotoxicity or antiproliferative activity. Therefore, the induction of cell cycle arrest and/or apoptosis is the major target for the development of an anticancer agent.

Cell cycle is composed of four phases which are G1, S, G2 and M. G1 phase is the period for the synthesis of proteins necessary for cell growth, specifically enzymes and structural proteins for cell division. S phase is the period for synthesis of intracellular DNA. G2 phase is the period for the preparation of mitosis. And M phase is the period for cell division including nuclear division and cytokinesis. When G1 phase is unnecessarily extended so that cell division is suspended, it is called G0 phase. In general, the whole cell division period depends on the length of G1 phase. Cancer cells are constantly proliferated and the period of G0/G1 phase of cancer cells is shorter than that of normal cells, suggesting that their cell division is very fast. So, it is one way to inhibit cancer cell growth separately from normal cells to treat a drug that is able to arrest cell cycle in a specific phase which is repeated fast in the case of cancer cells.

Daurinol, an arylnaphthalene lignan, is a single chemical component, which was first isolated from *Haplophyllum dauricum*, the medicinal plant of Mongolia, by the present inventors in early 1980s. The daurinol was also isolated from *Haplophyllum cappadocicum*, same family but a different plant. However, its pharmacological activity has never been reported yet. *Haplophyllum* sp. plants are perennial grasses and widely spread in central Asia. They have been used for the traditional folk remedy for various diseases over hundreds of years.

The present inventors completed this invention by confirming that daurinol isolated from the Mongolian medicinal plant *Haplophyllum dauricum* could arrest cell cycle of cancer cells selectively at S phase, induce apoptosis and reveal the cell toxicity stepwise and therefore it can be effectively used for the production of a novel cell cycle blocker, a novel apoptosis inducer, a novel cytotoxic agent, a pharmaceutical composition for the prevention and treatment of cancer.

DISCLOSURE

Technical Problem

An object of the present invention is to provide a pharmaceutical composition for the prevention and treatment of cancer comprising daurinol isolated from the Mongolian medicinal plant, *Hapophyllum dauricum*, or *Haplophyllum cappadocicum*.

Technical Solution

To achieve the above object, the present invention provides a *Haplophyllum dauricum* extract for the prevention and treatment of cancer.

The present invention also provides a pharmaceutical composition for the prevention and treatment of cancer comprising the *Haplophyllum dauricum* extract as an active ingredient.

The present invention further provides a pharmaceutical composition for the prevention and treatment of cancer comprising daurinol as an active ingredient.

The present invention also provides a cell cycle blocker comprising daurinol as an active ingredient.

The present invention also provides an apoptosis inducer comprising daurinol as an active ingredient.

The present invention also provides a cytotoxic agent comprising daurinol as an active ingredient.

The present invention also provides a use of the *Haplophyllum dauricum* extract or daurinol for the production of a preventive and therapeutic agent for cancer.

ADVANTAGEOUS EFFECT

The *Haplophyllum dauricum* extract has the cancer cell growth inhibitory effect. Daurinol isolated from *Haplophyllum dauricum* or *Haplophyllum cappadocicum* can induce cell cycle arrest at S phase selectively, disturb the cell cycle and then induce apoptosis of the cancer cells, resulting in anticancer activity. Thus, the *Haplophyllum dauricum* extract of the present invention can be used as a composition for the prevention and treatment of cancer. Daurinol, which can act as a novel cell cycle blocker and a novel apoptosis inducer, can be used as a positive control chemical in research and development field of cancer biology especially for cancer therapy and prevention. And also daurinol is a new type of highly valuable medicinal product applicable for the prevention and treatment of cancer.

DESCRIPTION OF DRAWINGS

The application of the preferred embodiments of the present invention is best understood with reference to the accompanying drawings, wherein.

BEST MODE

Hereinafter, the present invention is described in detail.

The present invention provides a *Haplophyllum dauricum* (L.) G. Don. extract for the prevention and treatment of cancer.

The *Haplophyllum dauricum* (L.) G. Don. was collected in the Gobi mountains in Uvurkhangaiskii aimak in Mongolia and Ulaanbaatar in Mongolia. The solvent for the extraction was ethanol. The present inventors extracted *Haplophyllum dauricum* first and then obtained the dry *Haplophyllum dauricum* extract by vacuum distillation. The *Haplophyllum dauricum* extract, a polar solvent soluble extract, of the present invention was obtained by a method selected from the group consisting of enfleurage, hot water extraction, ultrasonic extraction and reflux extraction with a polar solvent having approximately the volume of 1-10 times *Haplophyllum dauricum*, preferably approximately 1-3 times, selected from a group consisting of water, alcohol and a mixture thereof, more preferably with $C_1$-$C_3$ low alcohol, at room temperature for 1-2 days, preferably for one day.

The present invention also provides a pharmaceutical composition for the prevention and treatment of cancer comprising the *Haplophyllum dauricum* extract as an active ingredient.

To investigate the inhibitory effect of the *Haplophyllum dauricum* extract on the inhibition of cancer cell growth, the present inventors performed following experiments using human colon cancer cell lines. As a result, the *Haplophyllum dauricum* extract prepared from the plants collected in the two different areas in Mongolia did inhibit significantly the cancer cell growth dose-dependently (see Table 1 and FIG. 1). Therefore, the inventors confirmed that the *Haplophyllum dauricum* extract of the invention can be effectively used for the prevention and treatment of cancer.

The composition can be administered orally and be used in general forms of pharmaceutical formulation. Preferable formulations for oral administration are tablets, soft or hard capsules, liquids, suspensions, etc. These formulations are prepared by mixing the composition of the invention with pharmaceutically acceptable, generally used carriers such as excipients, binders, disintegrating agents, lubricants, solubilizers, suspending agents, preservatives or diluents.

The composition can include the *Haplophyllum dauricum* extract alone or include any pharmaceutically acceptable carriers or excipients in addition to the extract according to the types of formulations and application methods. At this time, the content of the *Haplophyllum dauricum* extract in the composition is preferably 0.001-50 weight %. If the content of the extract is less than 0.001 weight %, its effect as a pharmaceutical composition will be in doubt unless it is administered massively. On the contrary, if the content is more than 50 weight %, the effect will be constant but not increase even with such a massive amount, which means the administration is not economical. So, the content of the extract is preferably regulated according to the purpose and the method of the use.

The composition of the present invention can be administered singly or treated along with surgical operation, hormone therapy, chemotherapy and biological reactive regulator, to prevent and treat cancer.

The present invention further provides a pharmaceutical composition for the prevention and treatment of cancer comprising daurinol as an active ingredient.

An arylnphthalene lignan, daurinol of the present invention is a single chemical component, originated from the Mongolian medicinal plant *Haplophyllum dauricum* or *Haplophyllum cappadocicum*, which is represented by the following formula 1.

Formula 1

The *Haplophyllum dauricum* (L.) G. Don. was collected in Uvurkhangaiskii aimak of Mongolia and extracted with ethanol. Daurinol exists mostly in the aerial part of the plant but can be isolated from the root, too. The extract was fractionated by using petroleum ether, chloroform, ethylacetate and butanol. Particularly, chloroform fraction was separated by silica gel column (1:10) and eluted using different ratios of benzene-chloroform solvent. Daurinol was separated by fractional recrystallization using methanol as a solvent. The structure of daurinol was confirmed by various spectroscopic approaches including UV-spectrosocpy, IR-spectrosocpy, mass spectrosocpy, and 1H-NMR spectrosocpy.

Daurinol of the present invention can be isolated from *Haplophyllum* sp. plants such as *Haplophyllum dauricum* or *Haplophyllum cappadocicum* by the above method or synthesized by the conventional chemical synthesis method known to those in the art.

To measure the cytotoxicity of daurinol against cancer cells, MTT (methylthiazol-2-yl-2.5 diphenyl tetrazolium bromide) assay was performed using colon cancer cell lines HCT116 and DLD-1. As a result, daurinol showed a strong cytotoxicity against both cell lines and the inhibition of cancer cell growth was dose-dependent. The cell growth inhibitory effect was greater in 48 hour-treatment group than in 24-hour treatment group (see Table 2 and FIG. 2).

The colon cancer cell lines treated with daurinol were fixed and DNA was selectively stained with propidium iodide (PI), and then were analyzed by flow cytometry to investigate cell cycle. As a result, it was confirmed that daurinol induced cell cycle arrest at S phase (see FIGS. 3, 4 and 5). This result indicates that daurinol can be effectively used as a cell cycle blocker.

Figure 3:
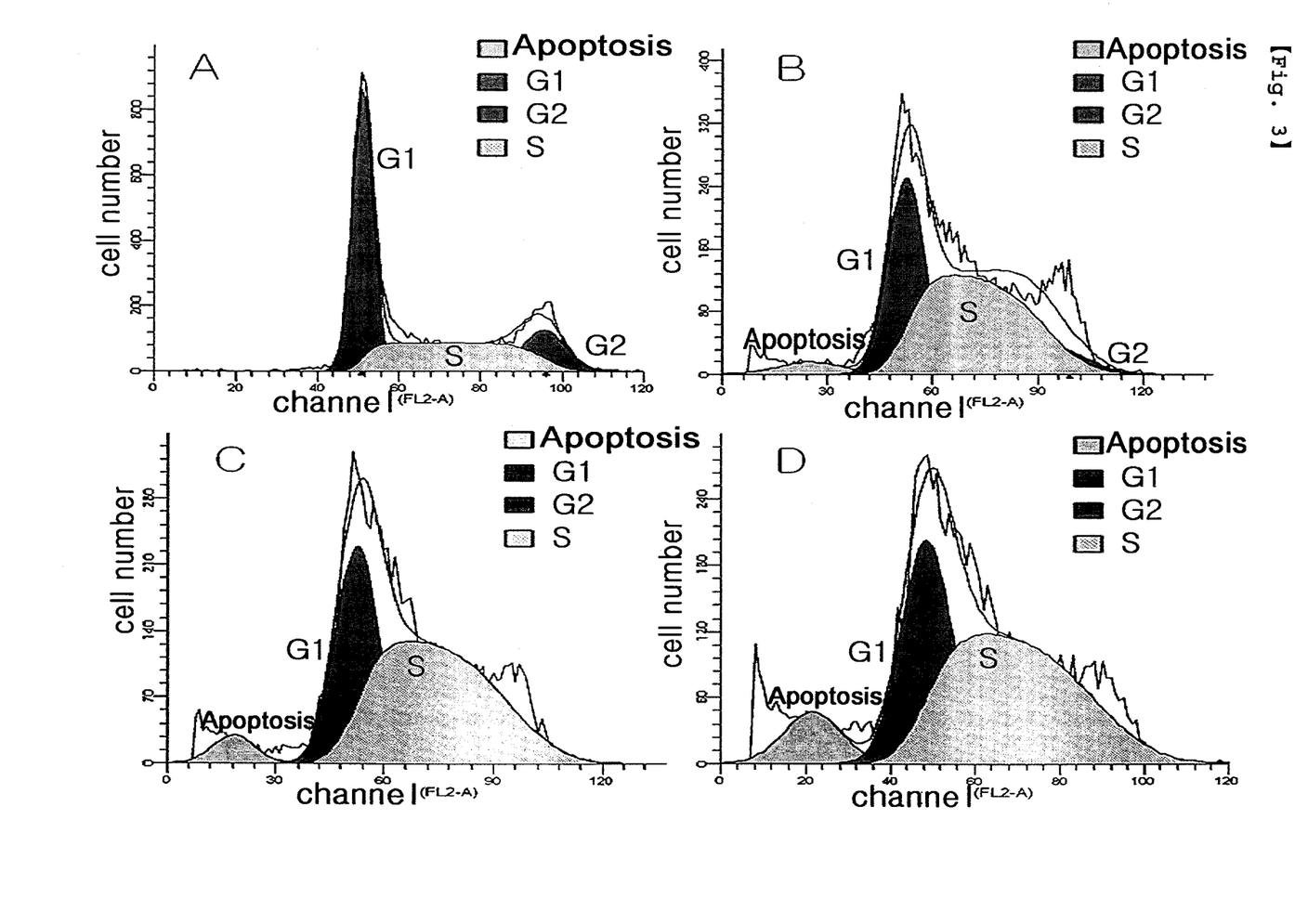
FIG. 3 is a graph illustrating the changes of cell cycle of a human colon cancer cell line (HCT116) treated with the different concentrations of daurinol:
  A: control;
  B: treated with 5 μM of daurinol;
  C: treated with 10 μM of daurinol; and
  D: treated with 20 μM of daurinol.
Figure 4:
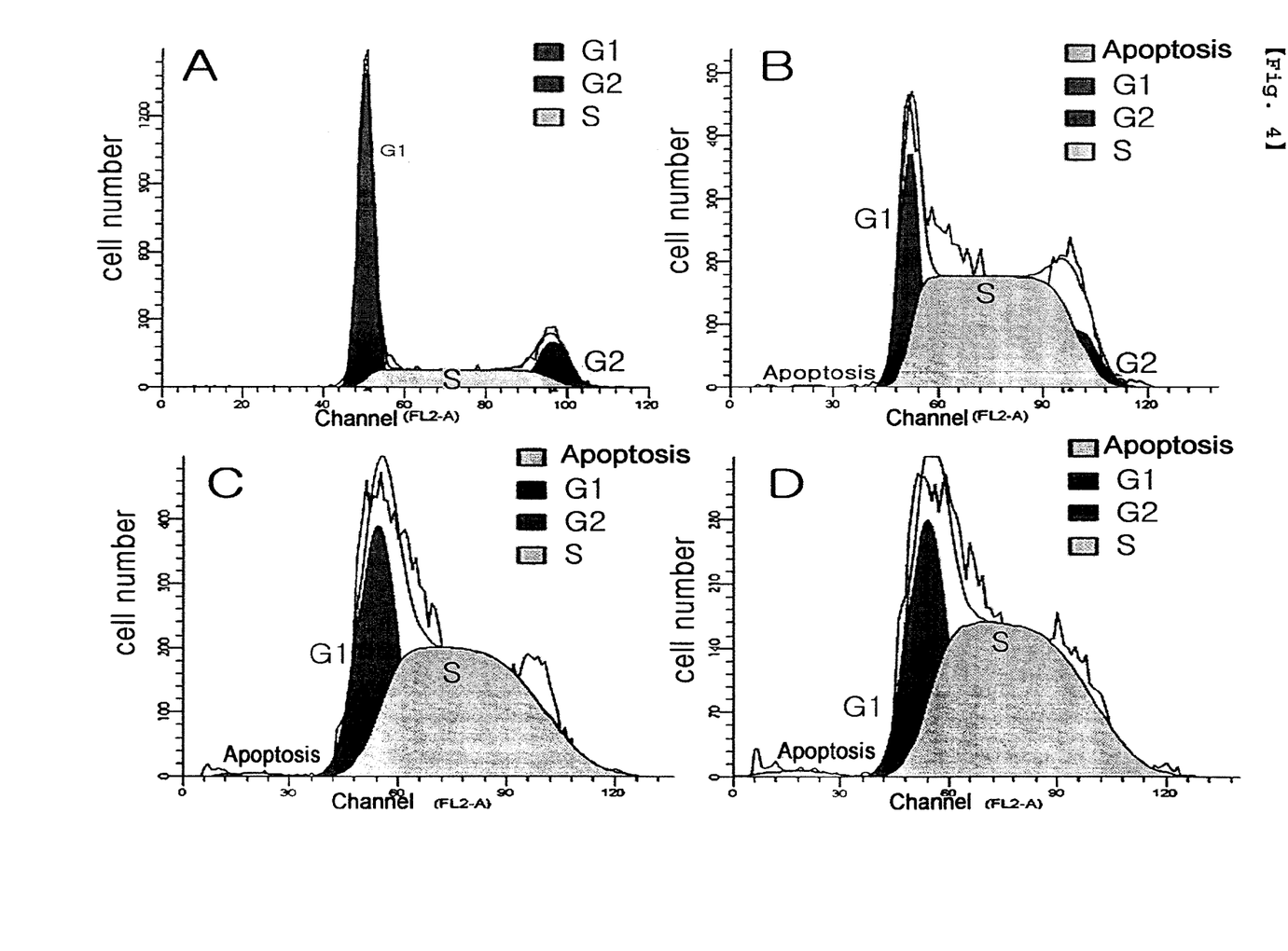
FIG. 4 is a graph illustrating the changes of cell cycle of a human colon cancer cell line (DLD-1) treated with the different concentrations of daurinol:
  A: control;
  B: treated with 5 μM of daurinol;
  C: treated with 10 μM of daurinol; and
  D: treated with 20 μM of daurinol.
Figure 6:
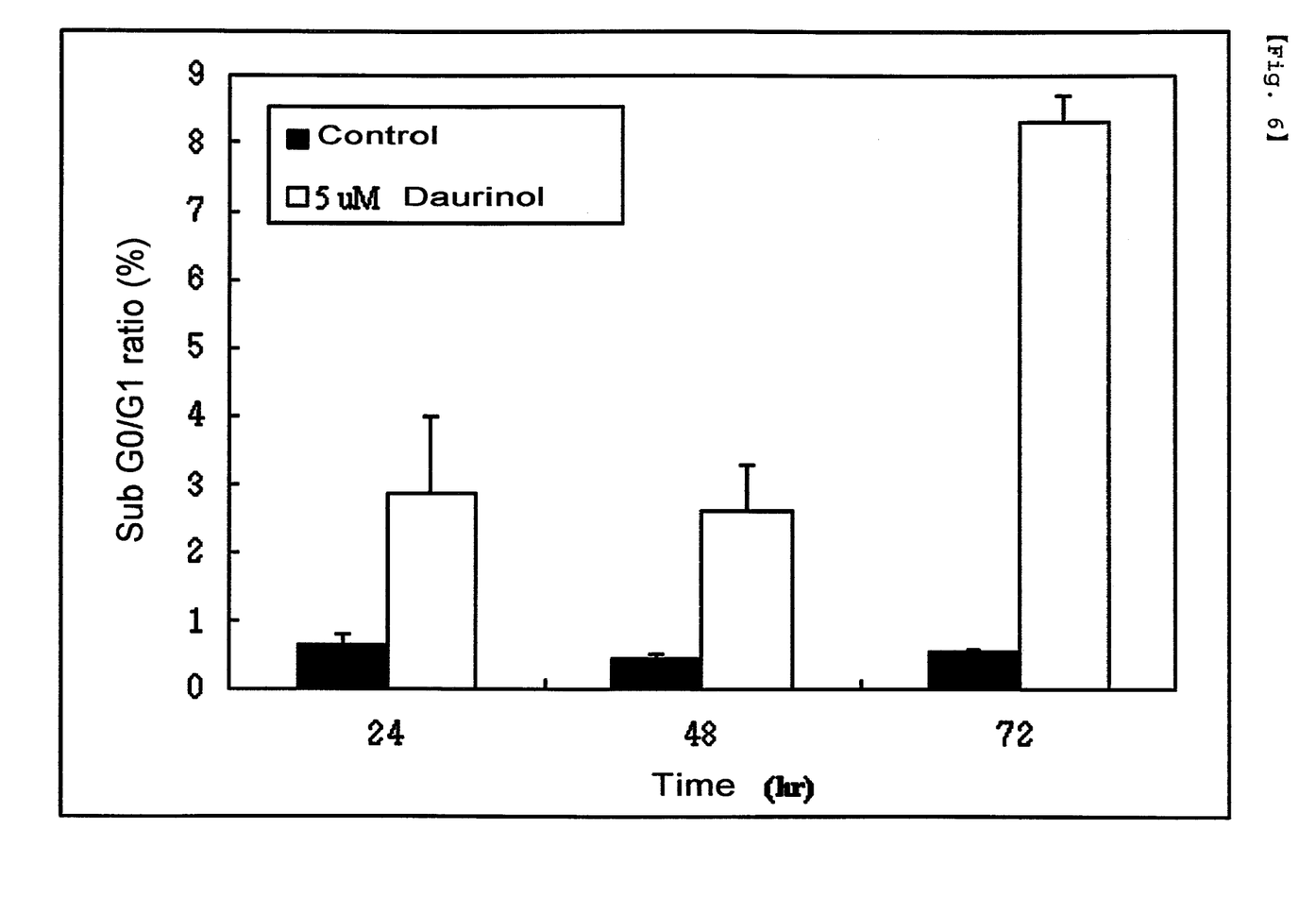
FIG. 6 is a graph illustrating the changes of sub G0/G1 ratio, the index for apoptosis, in a human colon cancer cell line (HCT116) at different treatment times of daurinol.

The present inventors also confirmed the sub G0/G1 ratio, the index of apoptosis by using cell cycle analysis, was significantly increased in the daurinol treated group (see Table 3 and FIG. 6). Sub G0/G1 indicates the period having less DNA than G0/G1 phase (for example, the front part or left of G0/G1 peak in the graph showing cell cycle). In FIGS. 3 and 4, the sign "apoptosis" indicates sub G0/G1. The first peak indicates G0/G1 phase and the middle part indicates S phase and the second peak indicates G2/M phase.

Cancer cells treated with daurinol were obtained, which were co-stained with annexin V-FITC (fluorescein isothiocyanate) and propidium iodide. The population of the early apoptotic cells was significantly increased in the daurinol treated group, compared with the control (see FIGS. 7 and 8). This result indicates that daurinol can be effectively used as an apoptosis inducer.

The cancer cell line was treated with daurinol and observed under DIC (differential interference contrast) light microscope 24 hours later. As a result, the boundary of the cells became obvious resulting in that a distance between the cells was getting apart. The cancer cell line was observed again under DIC light microscope 48 hours after the daurinol treatment. As a result, cancer cells were started to detach from the bottom of culture dish. At 72 and 96 hours after the treatment, this phenomenon was more apparent (see FIG. 9). This result indicates that daurinol exerts a cytotoxic effect especially through apoptosis induction.

As explained hereinbefore, daurinol of the present invention induces cell cycle arrest specifically at S phase and thereafter induces apoptosis, resulting in anticancer activity. Therefore, it can be effectively used for a pharmaceutical composition for the prevention and treatment of cancer.

The cancer herein can be selected from the group consisting of laryngeal cancer, lung cancer, esophageal cancer, pancreatic cancer, large intestine cancer, liver cancer, stomach cancer, tongue cancer, skin cancer, brain cancer, uterine cancer, breast cancer, cervical cancer, ovarian cancer, kidney cancer, gallbladder cancer, oral cancer, colon cancer and bladder cancer, and is preferably colon cancer, but not always limited thereto.

The composition of the present invention can be administered orally and be used in general forms of pharmaceutical formulation. The composition of the invention can additionally include, in addition to daurinol, one or more active ingredients having the same or similar functions. The composition of the present invention can also include, in addition to the above-mentioned active ingredients, one or more pharmaceutically acceptable carriers for the administration. The pharmaceutically acceptable carrier can be selected or be prepared by mixing more than one ingredients selected from the group consisting of saline, sterilized water, buffered saline, dextrose solution, maltodextrose solution, glycerol and ethanol. Other general additives such as anti-oxidative agent, buffer solution, bacteriostatic agent, etc, can be added. Also, in order to prepare powders, tablets, capsules, granules or granules such as solutions, suspension and emulsions, diluents, dispersing agents, surfactants, binders and lubricants can be additionally added. The composition of the present invention can further be prepared in suitable forms for each disease.

The composition of the invention can include daurinol alone or include any pharmaceutically acceptable carriers or excipients in addition to the extract according to the types of formulations and application methods. At this time, the content of the daurinol in the composition is preferably 0.001-50 weight %. If the content of daurinol is less than 0.001 weight %, its effect as a pharmaceutical composition will be in doubt unless it is administered massively. On the contrary, if the content is more than 50 weight %, the effect will be constant but not increase even with such a massive amount, which means the administration is not economical. So, the content of daurinol is preferably regulated according to the purpose and the method of the use The present invention also provides a cell cycle blocker, an apoptosis inducer and a cytotoxic agent comprising daurinol as an active ingredient.

As explained hereinbefore, daurinol of the invention induces cell cycle arrest specifically at S phase, so that it can be effectively used as a cell cycle blocker. It can also induce apoptosis so that it can be used for the apoptosis inducer as well.

The present invention also provides a method for the prevention and treatment of cancer comprising the step of administering the *Haplophyllum dauricum* extract or daurinol to subjects.

The subjects can be mammals and human is preferred. The *Haplophyllum dauricum* extract or daurinol can be locally or systemically administrated through various pathways including hypodermic injection, intramuscular injection or intravenous injection, etc.

The effective dosage of the *Haplophyllum dauricum* extract or daurinol of the present invention can be determined according to severity of a disease and condition, age, gender and complications of a patient. In general, the dosage is 10 mg-2 g per day (for an adult of about 50 kg in weight), and preferably 100 mg-0.5 g per day. The unit formulation can contain the daily dose or ½, ⅓, ¼ of the daily dose of the *Haplophyllum dauricum* extract or daurinol. Administration frequency is once-6 times a day.

The present invention also provides a method to induce cell cycle arrest, to induce apoptosis and to induce cytotoxic activity comprising the step of administering daurinol to cancer cells.

The cancer cells herein can be selected from the group consisting of cancer cells of laryngeal cancer, lung cancer, esophageal cancer, pancreatic cancer, large intestine cancer, liver cancer, stomach cancer, tongue cancer, skin cancer, brain cancer, uterine cancer, breast cancer, cervical cancer, ovarian cancer, kidney cancer, gallbladder cancer, oral cancer, colon cancer and bladder cancer. In a preferred embodiment of the present invention, human colon cancer cell lines HCT116 and DLD-1 were used.

In addition, the present invention provides a use of the *Haplophyllum dauricum* extract or daurinol for the production of a preventive and therapeutic agent for cancer.

The *Haplophyllum dauricum* extract or daurinol of the present invention was confirmed to have excellent cancer cell growth inhibitory effect in human colon cancer cell lines HCT116 and DLD-1, so that *Haplophyllum dauricum* extract or daurinol can be effectively used for the production of a preventive and therapeutic agent for cancer.

The agents can include the *Haplophyllum dauricum* extract or daurinol alone or include any pharmaceutically acceptable carriers or excipients in addition to the extract according to the formulations and application methods. At this time, the content of the extract or daurinol in the composition is preferably 0.001-50 weight %. If the content of the extract or daurinol is less than 0.001 weight %, its effect as a pharmaceutical composition will be in doubt unless it is administered massively. On the contrary, if the content is more than 50 weight %, the effect will be constant but not increase even with such a massive amount, which means the administration is not economical. So, the content of the *Haplophyllum dauricum* extract or daurinol is preferably regulated according to the purpose and the method of the use.

MODE FOR INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

EXAMPLE 1

Preparation of *Haplophyllum Dauricum* Extract

*Haplophyllum dauricum* (L.) G. Don. was collected in Gobi mountains of Uvurkhangaiskii aimak in Mongolia (Extract 1) and Ulaanbaatar in Mongolia (Extract 2). The plants were dried and pulverized. Extraction was performed 10 times with 6.5 kg of the pulverized *Haplophyllum dauricum* using ethanol as a solvent. The extract was concentrated by vacuum distillation.

The concentrated ethanol extract was dissolved in DMSO (Dimethyl Sulfoxide) to adjust the concentration to 20 mg/ml.

EXAMPLE 2

Preparation of Daurinol

The concentrated ethanol extract obtained in Example 1 was diluted with the same volume of distilled water to ethanol (1:1), followed by fractionation using several solvents. As a result, 261 g of fraction was obtained from petroleum ether layer, 126 g of fraction was obtained from chloroform later, 20 g of fraction was obtained from ethylacetate layer and 258 g of fraction was obtained from butanol later. Chloroform fraction was isolated by silica gel column (1:10), and eluted using different ratios of benzene-chloroform solvent. 0.82 g of daurinol was obtained by fractional recrystallization using methanol as a solvent.

Melting point of the recrystallized daurinol was 256-257° C. The daurinol was proceeded to thin layer chromatography using Silufol UV-254 plate and chloroform-ethylacetate (19:1) as a moving phase. As a result, Rf was 0.54. The structure of daurinol was also investigated by various spectroscopic approaches. As a result, the structure of daurinol was identified as shown in formula 1.

<Formula 1>

UV-spectrum of daurinol was investigated by using EPS-3T spectrometer, resulting in $\lambda^{ethanol}_{max}$ 227, 262, 296, 324, 352 nm (log ϵ 4.55, 4.68, 4.07, 4.09, 3.41). IR-spectrum was investigated by using UR-20 spectrophotometer, and as a result the absorption bands (cm$^{-1}$) were detected at 3390 (hydroxy group), 1762 (C=O), 623, 1600 (aromatic nucleus), 936 (—OCH$_2$O) and 777 (1,2,4-trisubstituted benzene ring). Mass spectrum was also investigated by using Mkh-1303 spectrometer and as a result m/e (relative abundance %): M$^+$ 350 (100), M-CHO 321 (10, m* 350→321, 294, 5), M-CO$_2$H 305 (10), M-C$_2$H$_2$O$_2$ 292 (4), M-CH$_3$OCO 291 (15), 278 (4), 277 (11), 264 (5), 263 (13), 251 (6), 249 (5), 248 (6), 235 (5), 233 (7), 221 (6), 220 (8), 205 (5), 192 (6), 176 (7), 175 (4), 165 (7), 164 (6), 163 (13), 160 (11), 146 (6).

50 mg of daurinol was reacted with 2 ml of acetic anhydride in the presence of 0.5 ml of pyridine at room temperature for 24 hours, leading to acetylation of daurinol. $^1$H-NMR spectrum was investigated by using JNM-4H-100 spectrometer, resulting in 2.30 (3H, s, Ar—OCOCH$_3$), 2.67 (3H, s, Ar—OCH$_3$), 5.24 (2 H, s, Ar—CH$_2$O—), 5.92 and 5.98 (1 H each, dd, $J_{gem}$=1.2 Hz, Ar—OCH$_2$O), 6.74 (1 H, br. s, H-2/), 6.70 (1 H, q, 8.4 and 1.5 Hz, H-6), 6.86 (1H, d, 8.5 Hz, H-5), 7.08 and 7.46 (1 H, s, each, H-5 and H-8), and 7.62 (1 H, br, s H-4). For the $^1$H-NMR spectrum analysis, chloroform (CDCl$_3$) substituted with deuterium was used as a solvent.

EXPERIMENTAL EXAMPLE 1

Cancer Cell Growth Inhibitory Effect of the *Haplophyllum dauricum* Extract

Extracts 1 and 2 obtained by the method of Example 1 were treated to human colon cancer cells to investigate the cancer cell growth inhibitory effect of these extracts.

Human colon cancer cell lines HCT116 (American type of cell culture, ATCC) and DLD-1 (American type of cell culture, ATCC) were cultured in MEM supplemented with 10% fetal bovine serum and antibiotics (penicillin and streptomycin) in a 37° C., 5% CO$_2$ incubator. Sub-culture was performed every 2-3 days. HCT116 and DLD-1 were inoculated in a 96-well plate at the concentration of 5×10$^3$ cells/well, followed by culture for 24 hours. The *Haplophyllum dauri-* cum extract dissolved in DMSO (Dimethyl Sulfoxide) was treated thereto at different concentrations of 1-200 μg/ml for 24 and 48 hours. Then MTT reagent (methylthiazol-2-yl-2.5 diphenyl tetrazolium bromide) was treated thereto. 1-3 hours later, $OD_{450}$ was measured to investigate cell growth.

Figure 1:
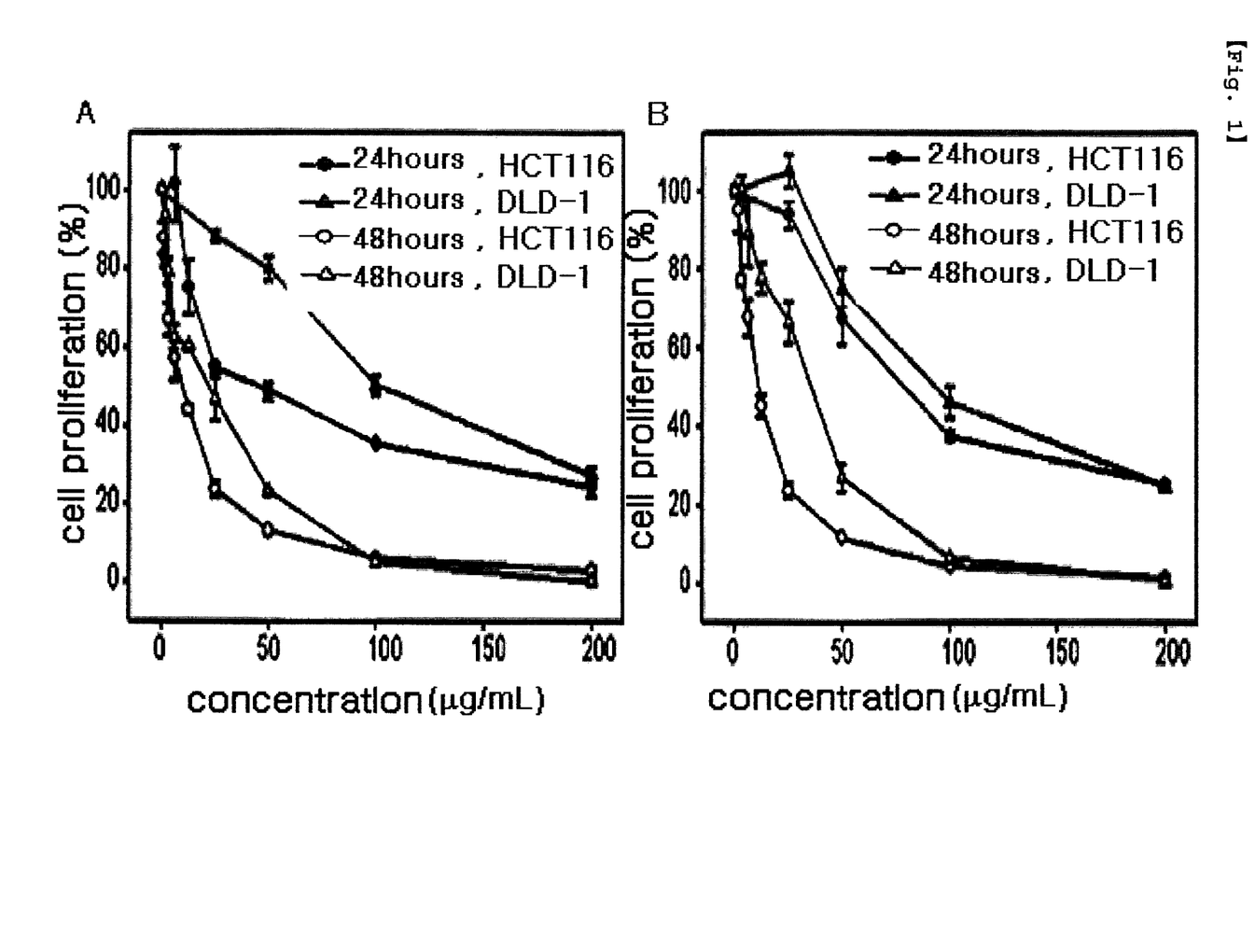
FIG. 1 is a graph illustrating the inhibition of cancer cell proliferation by the *Haplophyllum dauricum* extract:
A: Extract 1; and
B: Extract 2.

As a result, growth of the HCT116 and DLD-1 cell lines was significantly inhibited by Extracts 1 and 2, dose-dependently (Table 1 and FIG. 1). The cancer cell growth inhibitory effect of Extract 1 was greater than that of Extract 2. Both of the extracts exhibited stronger cancer cell growth inhibitory effect in HCT116 cell line than in DLD-1 cell line. The lower the $IC_{50}$, the higher the cytotoxicity was.

TABLE 1

The concentration for 50% of cell growth inhibition ($IC_{50}$) by the treatment of the *Haplophyllum dauricum* extract in colon cancer cell lines.

| | | $IC_{50}$ (μg/ml) | |
|---|---|---|---|
| Treatment time | Cell line | Extract 1 | Extract 2 |
| 24 hours | HCT116 | 48.4 | 84.1 |
| | DLD-1 | 102.8 | 98.3 |
| 48 hours | HCT116 | 8.1 | 11.3 |
| | DLD-1 | 14.7 | 27.5 |

EXPERIMENTAL EXAMPLE 2

Cancer Cell Growth Inhibitory Effect of Daurinol

Daurinol obtained by the method of Example 2 was treated to human colon cancer cell lines HCT116 (American type of cell culture, ATCC) and DLD-1 (American type of cell culture, ATCC) to investigate the cancer cell growth inhibitory effect. The cell lines were cultured in MEM supplemented with 10% fetal bovine serum and antibiotics (penicillin and streptomycin) in a 37° C., 5% $CO_2$ incubator. Sub-culture was performed every 2-3 days.

HCT116 and DLD-1 were inoculated in a 96-well plate at the concentration of $5 \times 10^3$ cells/well, followed by culture for 24 hours. Daurinol dissolved in DMSO (Dimethyl Sulfoxide) was treated thereto at different concentrations of 0.1-200 μg/ml for 24 and 48 hours. MTT reagent (methylthiazol-2-yl-2.5 diphenyl tetrazolium bromide) was treated thereto. 1-3 hours later, $OD_{450}$ was measured to investigate cell growth.

Figure 2:
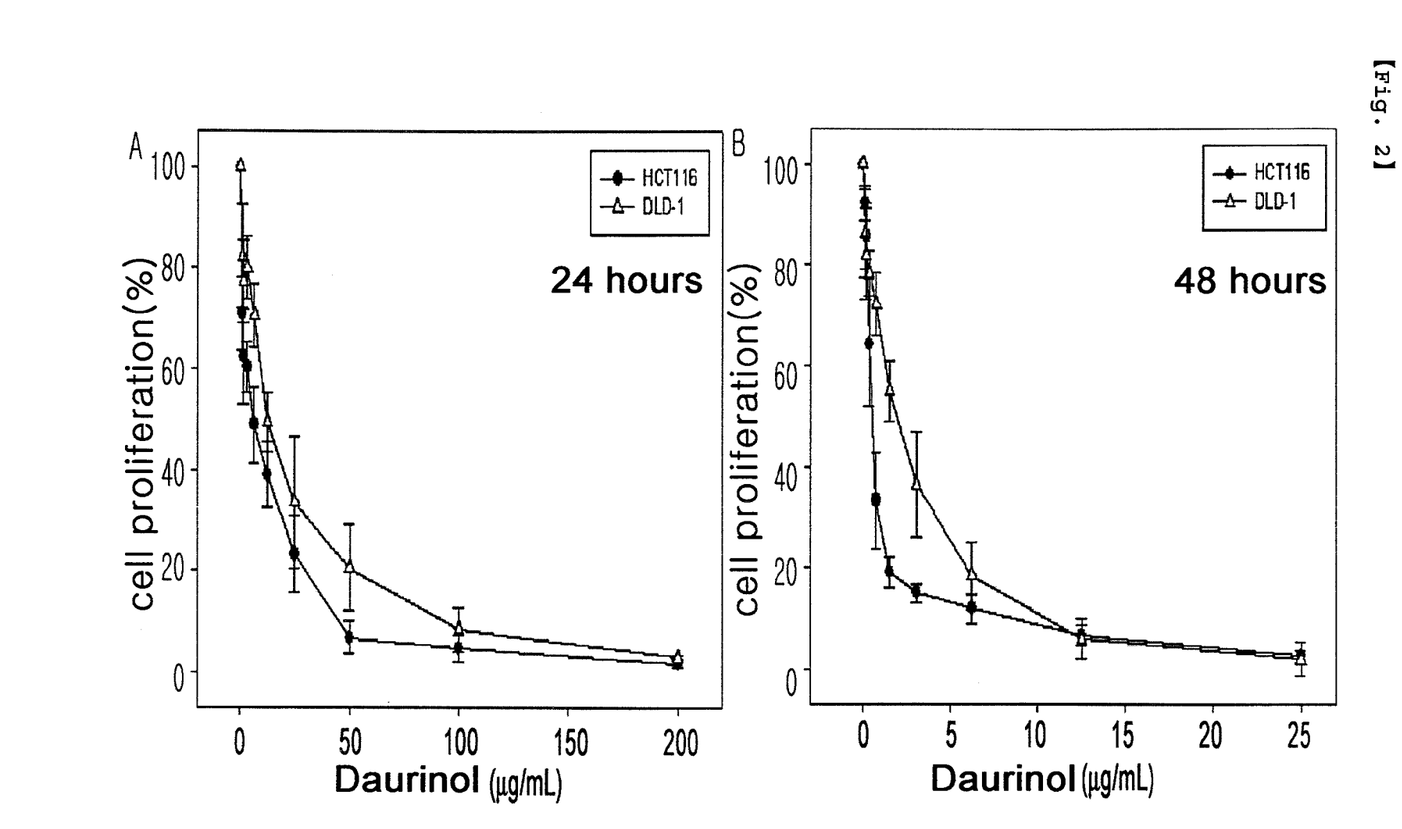
FIG. 2 is a graph illustrating the inhibition of cancer cell proliferation by daurinol:
  A: 24 hour treatment; and
  B: 48 hour treatment.

As a result, daurinol strongly inhibited the cancer cell growth in dose-dependent manner. Daurinol sensitivity was higher in HCT116 than in DLD-1. The cell growth inhibitory effect was higher when daurinol was treated for 48 hours than when it was treated for 24 hours (FIG. 2). After 24 hours from the daurinol treatment, cell cycle of the cancer cell line was arrested at S phase and after 48 hours from the treatment, apoptosis was clearly induced. $IC_{50}$ value (Concentration for 50% of cell growth inhibition) was obtained and shown in Table 2. The lower the $IC_{50}$ value, the stronger the cytotoxicity was. Cytotoxicity of daurinol was greater in HCT116 than in DLD-1.

TABLE 2

The concentration for 50% of cell growth inhibition ($IC_{50}$) by the treatment of daurinol in colon cancer cell lines.

| | | $IC_{50}$ | |
|---|---|---|---|
| Treatment time | Cell line | μg/ml | μM |
| 24 hours | HCT116 | 4.4 | 12.4 |
| | DLD-1 | 10.5 | 30.0 |
| 48 hours | HCT116 | 0.7 | 2.07 |
| | DLD-1 | 1.4 | 4.08 |

EXPERIMENTAL EXAMPLE 3

Daurinol as a Cell Cycle Blocker

Cell cycle blocking activity of daurinol obtained by the method of Example 2 was investigated.

Human colon cancer cell lines HCT116 and DLD-1 were inoculated in 60×15 cm culture dishes at the concentration of $5 \times 10^5$ cells per dish, followed by culture for 24 hours. Daurinol dissolved in DMSO (Dimethyl Sulfoxide) was treated thereto at the concentrations of 5-20 μM for 24, 48 and 72 hours, respectively. The cells were harvested and washed with DPBS (Dulbecco's Phosphate Buffered Saline), followed by fixation in 70% ethanol at −20° C. for more than one day. The cells were washed again with DPBS and stained with propidium iodide for 20 minutes, and then were analyzed by flow cytometry. The propidium iodide selectively stains intracellular DNA. So, the fluorescence by propidium iodide and cell numbers was used as variants to make a graph, showing the pattern of cell cycle. According to this graph, cell cycle blocking activity of daurinol and apoptosis induced by daurinol could be confirmed.

Daurinol was treated to HCT116 and DLD-1 at different concentrations (5, 10 and 20 μM) for 48 hours. As a result, S phase of cell cycle was significantly increased in the daurinol treated group, compared with the control group not treated with daurinol (FIGS. 3 and 4). The sub G0/G1 ratio which could be used as the index for apoptosis was increased significantly in the daurinol treated group, compared with the control not treated with daurinol, in particular the increase of the sub G0/G1 ratio was far more significant in HCT116 cell line than DLD-1 cell line (Table 3).

Figure 5:
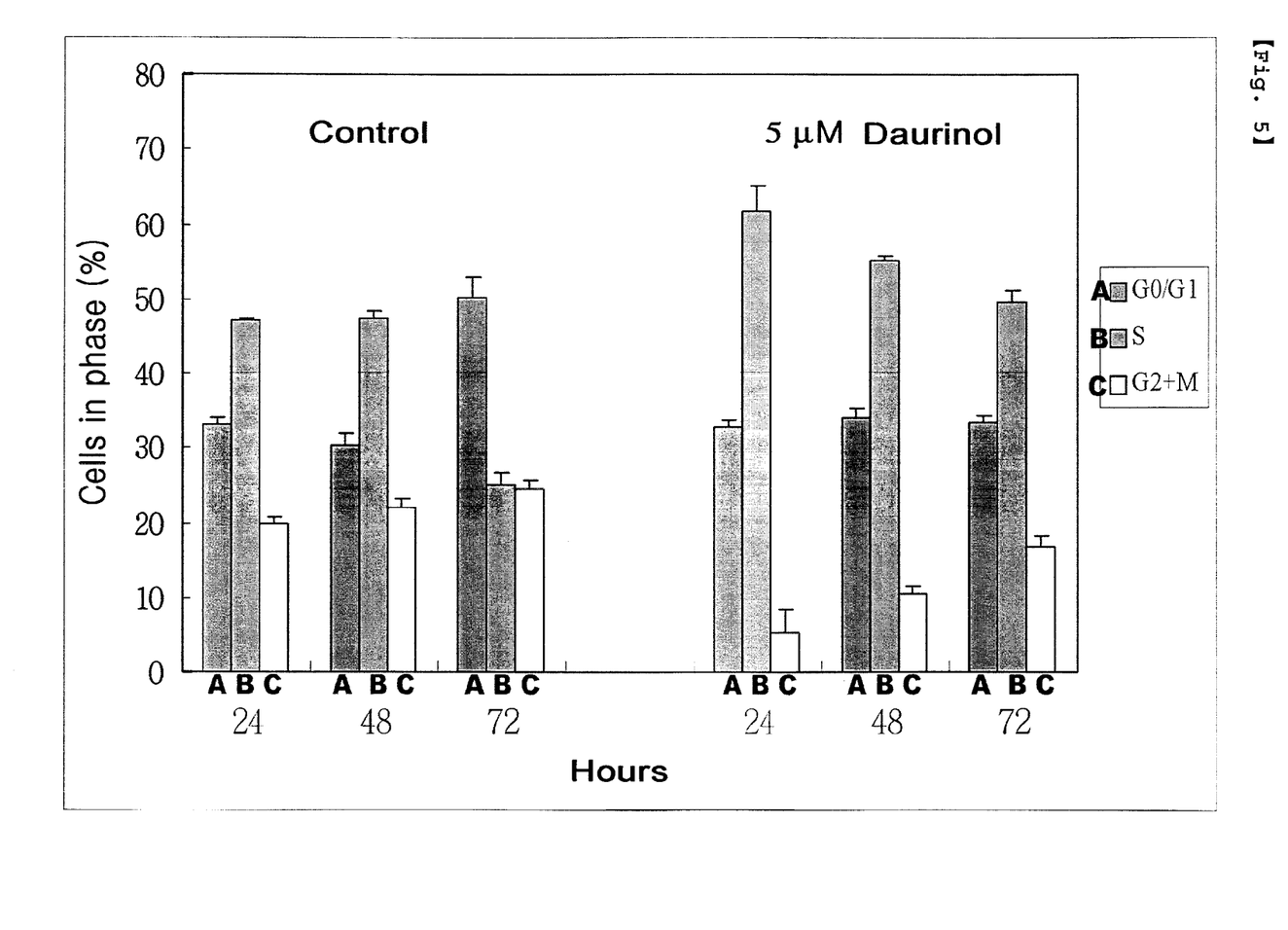
FIG. 5 is a graph illustrating the cell cycle phase (%) of a human colon cancer cell line (HCT116) at different treatment times of daurinol.

5 μM of daurinol was treated to HCT116 cell line for different times (24, 48 and 72 hours). As a result, S phase of cell cycle was significantly increased in the daurinol treated group, compared with the control not treated with daurinol (FIG. 5).

In addition, HCT116 cell line treated with 5 μM of daurinol, sub G0/G1 ratio, the index for apoptosis, was significantly increased (FIG. 6).

TABLE 3

Changes of cell cycle of cancer cell line by the treatment of daurinol at different concentrations for 48 hours (Ratios of S and sub G0/G1 phases in the graphs of FIG. 3 and FIG. 4)

| Cell cycle ratio (%) | Cell line | Control | 5 μM daurinol | 10 μM daurinol | 20 μM daurinol |
|---|---|---|---|---|---|
| S phase ratio | HCT116 | 33.7 | 52.8 | 61.1 | 60.8 |
| | DLD-1 | 29.6 | 68.6 | 64.1 | 68.0 |
| sub G0/G1 ratio | HCT116 | 0.1 | 3.8 | 4.6 | 9.4 |
| | DLD-1 | 0 | 0.3 | 0.6 | 1.4 |

EXPERIMENTAL EXAMPLE 4

Apoptosis Inducing Activity of Daurinol

The induction of apoptosis by daurinol obtained by the method of Example 2 was thoroughly examined by co-staining with annexin V—FITC (fluorescein isothiocyanate) and propidium iodide.

In normal cells, phosphatidylserine, one of the cell membrane forming phospholipids, is always heading toward inside of the cell. When early apoptosis is induced, this phosphatidylserine is exposed outside of the cell. Thus, the apoptotic cells can be detected by using green fluorescence labeled annexin V that is selectively bound to phosphatidylserine.

HCT116 cells were inoculated in 60×15 cm culture dishes at the concentration of $5 \times 10^5$ cells per dish, followed by culture for 24 hours. Daurinol dissolved in DMSO (Dimethyl Sulfoxide) was treated thereto at the concentrations of 5 µM for 24 and 48 hours. The cells were harvested and washed with DPBS (Dulbecco's Phosphate Buffered Saline). $1 \times 10^6$ cells were stained with annexin V-FITC (fluorescein isothiocyanate) and propidium iodide for 15 minutes, and then were analyzed by flow cytometry.

Figure 7:
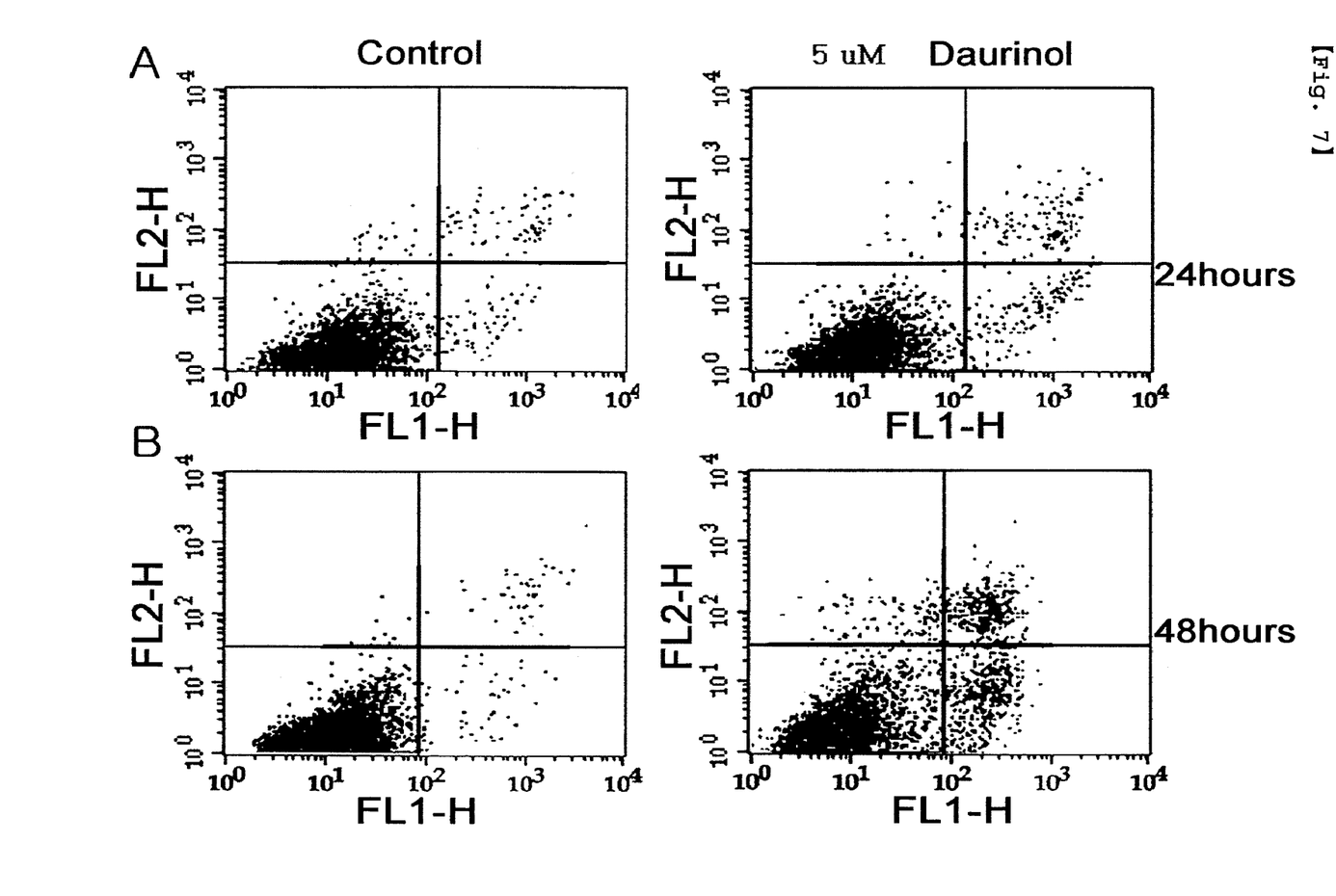
FIG. 7 is a diagram illustrating the apoptosis in a human colon cancer cell line (HCT116) treated with daurinol, for which the cells were stained with annexin V-FITC (fluorescein isothiocyanate) and propidium iodide, and then were analyzed by flow cytometry.
  A: 24 hour treatment; and
  B: 48 hour treatment.
Figure 8:
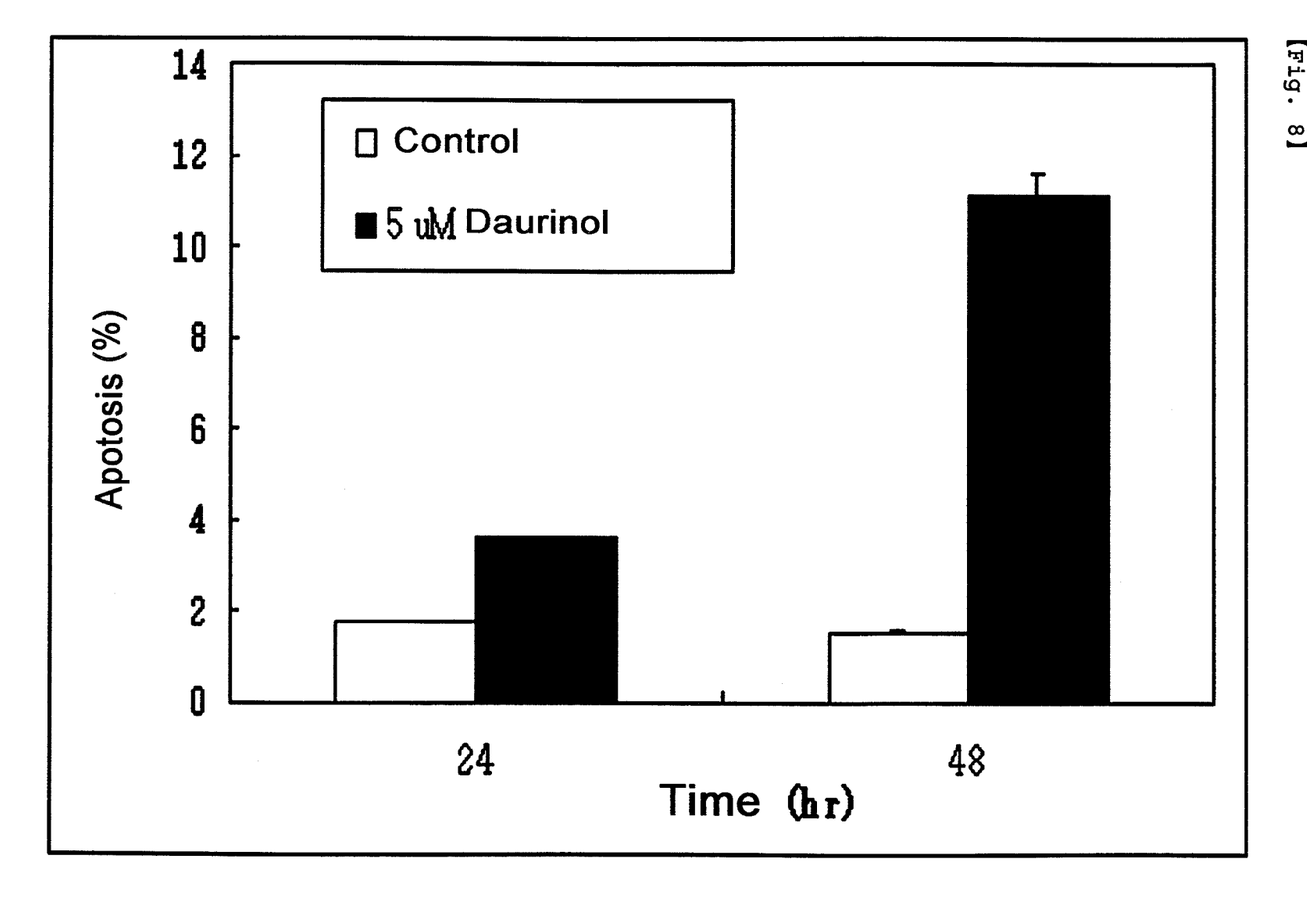
FIG. 8 is a graph illustrating the early apoptotic cell population in a human colon cancer cell line (HCT116) treated with daurinol. The percentage of the cells stained by annexin V-FITC but not by propidium iodide corresponds in the lower right quadrant of diagram in FIG. 6. represented by a bar graph.

As a result, apoptosis was significantly induced in HCT116 cells treated with 5 µM of daurinol, compared with the control (FIGS. 7 and 8). Apoptosis is apparently induced after 48 hr treatment of daurinol. This result indicates that daurinol induces cell cycle arrest at S phase and then induces apoptosis stepwise.

EXPERIMENTAL EXAMPLE 5

Morphological Changes of Cancer Cells by Daurinol

Daurinol obtained by the method of Example 2 was treated to cancer cells and then morphological changes of the cancer cells were observed under DIC (differential interference contrast) light microscope.

HCT116 cells were inoculated in 60×15 cm culture dishes at the concentration of $5 \times 10^5$ cells per dish, followed by culture for 24 hours. 5 µM of daurinol dissolved in DMSO (Dimethyl Sulfoxide) was treated thereto, followed by culture for 12, 24, 48, 72 and 96 hours respectively. Morphological changes of the cells were observed under DIC light microscope.

Figure 9:
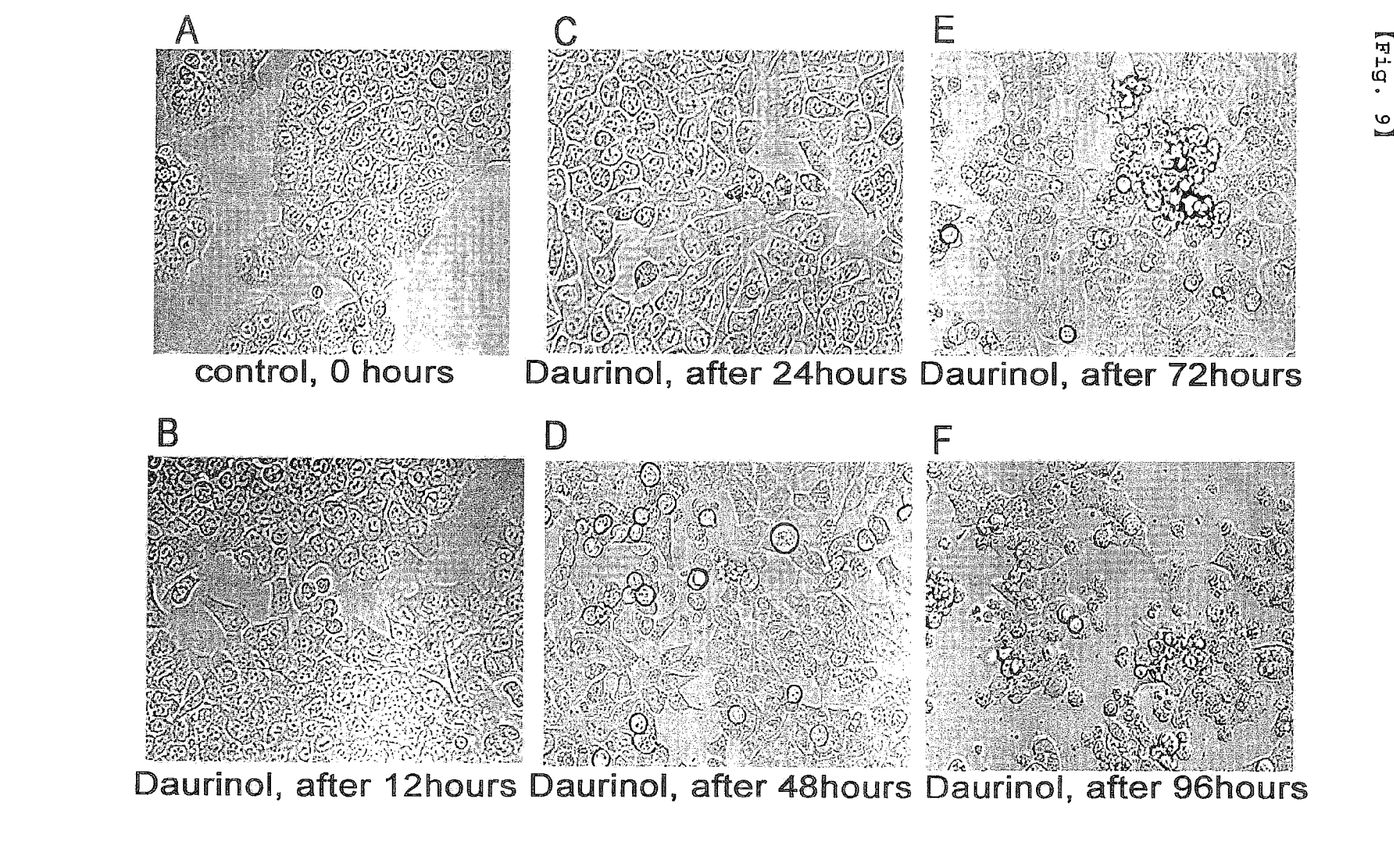
FIG. 9 is a diagram illustrating the morphological changes of a human colon cancer cell line (HCT116) by the treatment of daurinol:
  A: control, 0 hour;
  B: 12 hours after the treatment of daurinol;
  C: 24 hours after the treatment of daurinol;
  D: 48 hours after the treatment of daurinol;
  E: 72 hours after the treatment of daurinol; and
  F: 96 hours after the treatment of daurinol.

As a result, the boundary of the cells became obvious resulting in that a distance between the cells was getting apart in HCT116 cells after 24 hours from the treatment of daurinol. After 48 hours from the treatment, HCT116 cells were started to detach from the bottom of culture dish. After 72 hours and 96 hours from the treatment, the above phenomenon was more clearly detected (FIG. 9).

The Manufacturing Examples of the composition for the present invention are described hereinafter, but the present invention is not limited thereto.

MANUFACTURING EXAMPLE 1

Preparation of Pharmaceutical Formulations Comprising the *Haplophyllum dauricum* Extract as an Active Ingredient <1-1> Preparation of Soft Capsules Soft capsules containing 100.0 mg of the *Haplophyllum dauricum* extract prepared in Example 1, 175.0 mg of soybean oil, 45.0 mg of yellow beeswax, 127.5 mg of palm hardened oil, 21.0 mg of soybean phospholipid, 212.0 mg of gelatin, 50.0 mg of glycerin (specific gravity 1.24), 76.0 mg of D-sorbitol, 0.54 mg of paraoxymethylbenzoic acid, 0.90 mg of paraoxypropylbenzoic acid, 0.56 mg of methylvanillin and a proper amount of yellow food color 203 per capsule were prepared according to the manufacturing process of soft capsule of the Korean Pharmacopoeia.

<1-2> Preparation of Tablets 100.0 mg of the *Haplophyllum dauricum* extract prepared in Example 1, 90.0 mg of cornstarch, 175 mg of lactose, 15.0 mg of L-hydroxypropylcellulose, 5.0 mg of polyvinylpyrolidone90 and a proper amount of ethanol were mixed homogeneously and granulated by wet-granulating method. After adding 1.8 mg of magnesium stearin thereto, tablets were prepared containing 400 mg of the mixture per tablet.

<1-3> Preparation of Capsules 100.0 mg of the *Haplophyllum dauricum* extract prepared in Example 1, 83.2 mg of cornstarch, 175.0 mg of lactose and 1.8 mg of magnesium stearin were mixed homogeneously. And then, capsules were prepared containing 360 mg of the mixture per capsule.

MANUFACTURING EXAMPLE 2

Preparation of Pharmaceutical Formulations Comprising Daurinol as an Active Ingredient <2-1> Preparation of Powders

| | |
|---|---|
| Daurinol | 2 g |
| Lactose | 1 g |

Powders were prepared by mixing all the above components and filled airtight bags with the mixture.

<2-2> Preparation of Tablets

| | |
|---|---|
| Daurinol | 100 mg |
| Corn starch | 100 mg |
| Lactose | 100 mg |
| Magnesium stearate | 2 mg |

Tablets were prepared by mixing all the above components by the conventional method for preparing tablets.

<2-3> Preparation of Capsules

| | |
|---|---|
| Daurinol | 100 mg |
| Corn starch | 100 mg |
| Lactose | 100 mg |
| Magnesium stearate | 2 mg |

Capsules were prepared by mixing the components above and filled gelatin capsules with the mixture according to the conventional method for capsules.

<2-4> Preparation of Pills

| | |
|---|---|
| Daurinol | 1 g |
| Lactose | 1.5 g |
| Glycerin | 1 g |
| Xylitol | 0.5 g |

Pills were prepared containing 4 g of the mixture of the above components per pill by the conventional method for preparing pills.

<2-5> Preparation of Granules

| | |
|---|---|
| Daurinol | 150 mg |
| Soybean extract | 50 mg |
| Glucose | 200 mg |
| Starch | 600 mg |

All the above components were mixed. 100 mg of 30% ethanol was added thereto. Then, granules were prepared by drying the mixture at 60° C. and filled bags.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A method for treating colon cancer in a subject comprising administering an effective amount of daurinol to a subject in need thereof.

2. A method for inducing apoptosis comprising administering an effective amount of daurinol to cells.

3. The method according to claim 1, wherein the daurinol is isolated from *Haplophyllum dauricum* or *Haplophyllum cappadocicum*.

* * * * *